US007611726B2

(12) United States Patent
Yu

(10) Patent No.: US 7,611,726 B2
(45) Date of Patent: Nov. 3, 2009

(54) SHINE-ENHANCING FILM FORMERS

(75) Inventor: Wei Hong Yu, Edison, NJ (US)

(73) Assignee: L'Oréal (FR)

( * ) Notice: Subject to any disclaimer, the term of this patent is extended or adjusted under 35 U.S.C. 154(b) by 841 days.

(21) Appl. No.: 10/891,549

(22) Filed: Jul. 15, 2004

(65) Prior Publication Data

US 2006/0013839 A1 Jan. 19, 2006

(51) Int. Cl.
*A61K 8/02* (2006.01)
*A61Q 1/02* (2006.01)
*A61Q 19/04* (2006.01)
*A61Q 1/06* (2006.01)
*A61Q 1/04* (2006.01)

(52) U.S. Cl. .............................. 424/401; 424/63; 424/64

(58) Field of Classification Search ................. 424/401, 424/400, 63, 64
See application file for complete search history.

(56) References Cited

U.S. PATENT DOCUMENTS

| 4,536,405 | A | 8/1985 | Nara et al. |
| 4,699,780 | A | 10/1987 | Jennings et al. |
| 4,792,444 | A | 12/1988 | Fukasawa et al. |
| 5,075,103 | A | 12/1991 | Holloran et al. |
| 5,246,694 | A | 9/1993 | Birthwistle |
| 5,302,379 | A | 4/1994 | Sojka |
| 5,439,673 | A | 8/1995 | Murray |
| 5,654,362 | A | 8/1997 | Schulz, Jr. et al. |
| 5,817,302 | A | 10/1998 | Berthiaume et al. |
| 5,948,393 | A | 9/1999 | Tomomasa et al. |
| 6,180,123 | B1 | 1/2001 | Mondet |
| 6,309,629 | B1 * | 10/2001 | Travkina et al. .......... 424/78.03 |
| 6,423,306 | B2 | 7/2002 | Caes et al. |
| 6,461,626 | B1 | 10/2002 | Rabe et al. |
| 6,464,967 | B1 | 10/2002 | Collin |
| 6,503,521 | B1 | 1/2003 | Atis et al. |
| 6,514,504 | B1 | 2/2003 | Yen et al. |
| 6,517,818 | B1 | 2/2003 | Golz-Berner et al. |
| 6,517,823 | B1 | 2/2003 | Norman et al. |
| 6,531,142 | B1 | 3/2003 | Rabe et al. |
| 6,538,061 | B2 | 3/2003 | Chaiyawat et al. |
| 6,558,682 | B2 | 5/2003 | Yen et al. |
| 6,641,821 | B1 | 11/2003 | Collin et al. |
| 6,648,958 | B2 | 11/2003 | Anselmann et al. |
| 6,716,420 | B2 | 4/2004 | Feng et al. |
| 2001/0007654 | A1 | 7/2001 | Caes et al. |
| 2002/0004054 | A1 | 1/2002 | Calello et al. |
| 2002/0031488 | A1 | 3/2002 | Kanji et al. |
| 2002/0076425 | A1 | 6/2002 | Mondet et al. |
| 2002/0110573 | A1 | 8/2002 | Caes et al. |
| 2002/0114773 | A1 | 8/2002 | Kanji et al. |
| 2003/0003064 | A1 | 1/2003 | Kalla et al. |
| 2003/0003065 | A1 | 1/2003 | Kalla et al. |
| 2003/0017124 | A1 | 1/2003 | Agostini et al. |
| 2003/0082123 | A1 | 5/2003 | Anselmann et al. |
| 2003/0086883 | A1 | 5/2003 | Feng et al. |
| 2003/0161806 | A1 | 8/2003 | Arnaud et al. |
| 2003/0185782 | A1 | 10/2003 | Auguste et al. |
| 2003/0235552 | A1 | 12/2003 | Yu |
| 2003/0235600 | A1 | 12/2003 | Atis et al. |
| 2004/0009198 | A1 | 1/2004 | Bernard et al. |
| 2004/0009202 | A1 * | 1/2004 | Woller ........................ 424/401 |
| 2004/0042980 | A1 | 3/2004 | Kanji et al. |
| 2004/0086464 | A1 | 5/2004 | Riebe et al. |
| 2004/0086473 | A1 | 5/2004 | Rabe et al. |
| 2004/0096472 | A1 | 5/2004 | Tournilhac |
| 2004/0137028 | A1 * | 7/2004 | de la Poterie ............... 424/401 |
| 2004/0191197 | A1 | 9/2004 | Maio et al. |
| 2006/0013839 | A1 | 1/2006 | Yu |
| 2006/0134035 | A1 | 6/2006 | Zheng et al. |

FOREIGN PATENT DOCUMENTS

| CA | 2278685 | * | 8/1998 |
| EP | 0 205 760 | | 12/1986 |
| EP | 0 542 669 | | 5/1993 |
| EP | 0 787 730 | | 8/1997 |
| EP | 0 787 731 | | 8/1997 |
| EP | 1 208 836 A | | 5/2002 |
| JP | 52-90637 | | 1/1976 |
| JP | 58-052367 | | 3/1983 |
| JP | 60-155248 | | 8/1985 |
| JP | 62-054744 | | 3/1987 |
| JP | 62-172958 | | 7/1987 |
| JP | H04-305514 | | 10/1992 |
| JP | 09-012787 | | 1/1997 |
| JP | 2000-038315 | | 2/2000 |
| JP | 2002-154916 | | 5/2002 |
| JP | 2004-051850 | | 2/2004 |
| WO | WO-96/08537 | | 3/1996 |
| WO | WO 98/42298 | | 10/1998 |

OTHER PUBLICATIONS

Encyclopedia of Polymer Science and Technology vol. 3, Interscience, NY (1965).
Encyclopedia of Chemical Tech., Supp. Vol. Interscience, NY (1971).

(Continued)

*Primary Examiner*—Sreeni Padmanabhan
*Assistant Examiner*—Umamaheswari Ramachandran
(74) *Attorney, Agent, or Firm*—Lerner, David, Littenberg, Krumholz & Mentlik, LLP

(57) ABSTRACT

Shine-enhancing film formers are used to formulate cosmetic compositions in which shine is a desired property. Shine-enhancing film formers may be used alone for a high degree of shine or in combination with other film formers to modify the degree of shine. Using shine-enhancing film formers in cosmetics compositions often accomplishes increased shine properties while retaining other properties favorable to cosmetic compositions such as transfer-resistance.

8 Claims, No Drawings

OTHER PUBLICATIONS

International Cosmetic Dictionary and Handbook vol. 2.
European Search Report, EP 05 25 4410, Dated Oct. 28, 2005.
"Treated Pigments—May 2000"; Kobo Products, Inc. www.koboproducts.com; 20 pgs.
Wenninger, J. A. & McEwen, Jr., G. N. (1997). International Cosmetic Ingredient Dictionary and Handbook (pp. 72 and 142). Washington, DC: The Cosmetic, Toiletry, and Fragrance Association.
Koboguard 5400 IDD, Kobo Products. Jan. 1, 2004.
LIR, Kurarary Co., Ltd. Jan. 1, 2003.
Puresyn™ Polyalphaolefins: A Famiily of Versatile Emollients. 1/1/0.
Koboguard 5400: A Solid Hydrocarbon Resin for Long Wear Cosmetics. Dec. 4, 2003.

* cited by examiner

SHINE-ENHANCING FILM FORMERS

BACKGROUND OF THE INVENTION

High shine is a desirable characteristic for certain cosmetic compositions including lip products. However, in an effort to obtain other desirable properties, shine may be compromised. For example, several transfer resistant cosmetic compositions known in the art require the use of a complex composition in which the oils are partially replaced by volatile solvents which evaporate on contact with the skin, leaving a layer composed essentially of waxes and/or resins, pigments, fillers and actives. These compositions result in a powdery and matte appearance.

Currently, fillers, mother-of-pearl and pearling agents are most often used to augment shine properties in cosmetic compositions. (See, e.g., U.S. Pat. No. 6,423,306, column 7, ll. 14-23 (issued Jul. 23, 2002); U.S. Published Appln. No. 2002/0110573, p. 4, ¶ 38 (published Aug. 15, 2002). Certain types of polymers with indices of refraction of 1.5 or greater and oils have also been used as shine enhancers. (Patent Appln. Publication No. U.S. 2002/0004054, published Jan. 10, 2002, page 9, column 1, ¶¶ 0118-0122; page 8, column 1, ¶ 0094.) However, the principal polymers disclosed are generally polar and identified as, inter alia, polymers or copolymers of alkylated polyvinyl-pyrrolidone monomers, polyvinylpyrrolidone monomers or monoalkyl esters of poly (methylvinylether/maleic acid). Thus, additional ingredients may still be needed or certain formulation techniques may still be needed to increase or retain the shine.

A material useful in colored and clear cosmetic compositions that increases shine or mitigates overall reduction in shine properties, with a minimum impact on other desirable cosmetic properties, would overcome the limitations of the prior art. A shine-enhancer that can also provide other desirable benefits, thus reducing the number of ingredients needed in a cosmetic formulation would also be highly desirable.

SUMMARY OF THE INVENTION

The present invention involves the discovery that certain film formers can be produced which have shine-enhancing properties. The use of one or more of these shine-enhancing film formers in cosmetic compositions in which shine is desirable and specifically contemplated. Cosmetics through which color is delivered or deposited on the skin are most preferred. The use of these shine-enhancing film formers are particularly preferred for lip products such as lipsticks or glosses. It is understood that while many of such products are colored, some, such as certain glosses, are uncolored. Both are contemplated.

Preferably, these shine-enhancing film formers can be used in place of other film formers, non-film forming shine enhancers or at least some of both. Some of the shine-enhancing film formers of the invention may increase the degree of shine (or mitigate shine reduction) in a composition while promoting adherence of a composition to a substrate such as skin or hair.

The present invention contemplates a shine-enhancing film former comprising: at least one shine-enhancing polymer dissolved, dispersed, suspended, or emulsified in an organic solvent. In one embodiment of the present invention, the at least one shine-enhancing polymer is a low molecular weight non-polar, thermoplastic polyolefin. The shine-enhancing polymer may include at least one of C5+ olefin monomers, C5+ paraffin monomers or C5+ diolefin monomers, and, in another embodiment, $C_5$-$C_{20}$ polyolefins. These include hydrogenated polycyclopentadienes and hydrogenated $C_6$-$C_{20}$ polyolefins, as well as piperylene/butene/pentene copolymers such as those sold by Eastman Chemical Co. of Kingsport, Tenn., under the trade names EASTOTAC and PICCOTAC resin. In another embodiment, the shine-enhancing polymer includes at least one hydrogenated, inert thermoplastic resins derived from petrochemical feedstocks. These include certain hydrogenated polycyclopentadienes and hydrogenated styrene/methylstyrene/indene copolymers sold by Eastman Chemical Co. of Kingsport, Tenn. under the trade name REGALITE. In a preferred embodiment, the film former excludes appreciable amounts of alkylated polyvinyl pyrrolidone monomers, polyvinylpyrrolidone monomers or monoalkyl esters of poly(methylvinylether/maleic acid). Also useful as polyolefins in accordance with the present invention are PICCOLYTE® polyterpene hydrocarbon resins such as PICCOLYTE® A115, which is a polymer of alpha-pinene [CAS Reg. No. 31393-98-3] available from Hercules Inc. Resin Division, Hercules Plaza, 1313 North Market Street, Wilmington Del. 19894-0001.

In another embodiment, the at least one shine-enhancing polymer is a low molecular weight non-polar, thermoplastic polyolefin having a refractive index of less than 1.5 when measured at a temperature of between about 18 and about 25 degrees Centigrade. In another embodiment, it may have a refractive index of about 1.3 or less. The film former may have a molecular weight of about 5,000 or less.

Another aspect of the present invention is a cosmetic composition comprising: a shine-enhancing film former, itself comprising between about 0.5 and about 80% w/w of at least one low molecular weight non-polar, thermoplastic polyolefin shine-enhancing polymer dissolved, dispersed, suspended, or emulsified in an organic solvent. Also generally included in these cosmetic composition is at least one emulsifier, surfactant, fatty substance, wax, structuring agent, gelling agent, oil, preservative, viscosity increasing agent, moisturizing agent, co-solvent, emollient, dye, pigment, coloring agent, conventional shine enhancer, buffer, fragrance, non-shine-enhancing film former, conditioner, spreading agent, dispersant, antifoaming agent, wetting agent, UV-screening agent, UV filter, perfume, filler, cosmetically active agent, topical coating, moisturizer, vitamin or derivative thereof. The shine-enhancing polymer and the shine-enhancing film formers produced using same as described above are preferred for use in these cosmetic compositions. Preferred cosmetic compositions include lipsticks (which includes lipliners and pencils), lip glosses, eye liners, eye shadow, mascara and the like.

Certain embodiments of the present invention overcome some or all of the disadvantages of the prior art. Using shine-enhancing film formers in accordance with the invention may, in some instances, reduce or eliminate the need to add additional ingredients in a cosmetic composition to increase or maintain shine. Of course, if desirable, traditional shine-enhancing agents as well as non-shine-enhancing film formers may still be used in the cosmetic compositions of the present invention. Further, the shine-enhancing film formers of the present invention may instill and/or preserve shine while enhancing or minimally decreasing one or more other desirable qualities such as, without limitation, adherence to a substrate, flexibility, wearability, fast-drying, non-tacky, transfer-resistance, and low migration over time.

One cosmetic composition in accordance with the present invention is a lipstick (lipstick, lip liner or lip pencil) comprising a shine-enhancing film former itself comprising between about 0.5 and about 80% w/w, preferably between about 0.5 and about 30% w/w, of at least one low molecular weight non-polar, thermoplastic polyolefin shine-enhancing polymer dissolved, dispersed, suspended, or emulsified in a solvent. These cosmetic compositions also include at least one structuring agent, which may be, but is not limited to, a wax or thickener, and which is used in amount which is sufficient to produce a self-sustaining shape at room temperature, such as a stick, pencil, liner or eye shadow. Preferably, they also include at least one pigment. Particularly preferred are compositions with a viscosity that is greater than 300,000 centipoise(cP) at 25° C.

Also contemplated is a lip gloss. These comprise a shine-enhancing film former comprising between about 0.5 and about 80% w/w, preferably between about 0.5 and about 60% w/w of at least one low molecular weight non-polar, thermoplastic polyolefin shine-enhancing polymer dissolved, dispersed, suspended, or emulsified in an organic solvent. Also included is at least one viscosity increasing agent. Lip gloss will generally not include a structuring agent in an amount necessary to allow the composition to be formed into a self-sustaining shape such as a stick, liner or pencil. In a preferred embodiment, the lip gloss will also include at least one pigment. In a particularly preferred embodiment of this aspect of the present invention, the composition will have a viscosity of about 300,000 cP at 25° C.

DETAILED DESCRIPTION

"Polymer" used in connection with shine-enhancing polymers of the present invention includes polymers, copolymers and block copolymers of generally non-polar polyolefins. These are dissolved, dispersed, emulsified, suspended in a suitable solvent to produce a film former.

A "cosmetic composition" in accordance with the present invention is a cosmetic product that may be colored or uncolored, clear, translucent or opaque, applied to the skin or to facial hair, such as eye lashes, for the purpose of altering or enhancing appearance. While such products may additionally provide attributes such as cleansing, conditioning or protection from radiation, that is not their principle role. Cosmetic compositions are intended to exert their influence on the feel and/or appearance of skin and/or facial hair after it is applied, until it is removed or wears off. It is generally not intended to be applied and stripped away as in the case of a shampoo or many types of conditioners. This includes, without limitation, lip products such as lipstick (including lip pencils and lip liners), lip gloss or lip liner, mascara, eyeliner or eye shadow.

"Shine-enhancing" in accordance with the present invention means increasing shine or, as the case may be, mitigating or reducing any reduction in shine that may result from the use of corresponding amounts of non-shine enhancing film formers. This can be easily determined. Assuming that a shine-enhancing film former is used as described in the invention, it should, in a given formulation, provide an increased level of shine when compared to an identical formulation made with an equal amount of a non-shine-enhancing film former. Comparison may also be made against a reference standard. The relative shine of the formulation of the invention which includes a shine-enhancing film former versus an otherwise identical formulation without same can be measured by any known technique including, without limitation, the use of a gloss meter as described in U.S. Pat. No. 6,517,823 to Norman et al., assigned to L'OREAL, issued Feb. 11, 2003, and U.S. Pat. No. 6,716,420 to Feng et al., assigned to L'OREAL, issued Apr. 6, 2004, the texts of which, with regard to gloss meters and their uses, are hereby incorporated by reference.

"Gloss," as used herein (except when referring to a lip gloss), refers to surface shininess. Gloss meters are commonly used in the nail polish art as well as in other areas of cosmetics, and measure the amount of light reflected from the surface or film of interest. The gloss may be quantified, for example, as a % reflectance.

Where the present invention includes a cosmetic composition with an effective amount of at least one shine-enhancing film former or shine-enhancing polymer, "effective amount" is the amount of shine-enhancing film former or shine-enhancing polymer needed to achieve the desired degree of shine and/or adhesion in a final composition. At a minimum, this is an amount necessary to produce an objectively measurable higher level of shine in a cosmetic composition when compared to the same formulation including a like amount of a non-shine enhancing film former. In those formulations where shine-enhancing film formers are added to mitigate shine reduction, the relative degree of shine reduction is related to the effective amount of film former used. In these later instances, the degree of enhancement is maximum when no reduction is achieved.

Shine-enhancing film formers in accordance with the present invention are formulated by dissolving shine-enhancing polymers (including homopolymers, copolymers and block copolymers) in an appropriate solvent. The shine enhancing polymers of the present invention are polyolefins. These polyolefins are generally nonpolar and, at best, only slightly water soluble, if not substantially water insoluble.

In some embodiments, these shine enhancing polymers are thermoplastics and often have a low molecular weight. In preferred embodiments, but not in all embodiments, "low molecular weight" means, unless specified otherwise, that the weight average molecular weight of the shine-enhancing polymer is about 5,000 or less. In another embodiment, the weight average molecular weight is about 2,200 or less. In yet another embodiment, the weight average molecular weight is about 1,000 or less. Of course, a polyolefin that has a slightly higher molecular weight and is a polyolefin that can provide the advantages of the invention is also contemplated by the term "low molecular weight."

In an embodiment, shine-enhancing polymers have a refractive index of less than 1.5 when measured at between 18 and 25 degrees centigrade. In another embodiment, the shine-enhancing polymers have a refractive index of less than 1.3 when measured at between 18 and 25 degrees centigrade.

Shine-enhancing polymers include, without limitation, low molecular weight ($M_w$ between approximately 770 and 2200) thermoplastic polyolefins containing C5+ olefin, C5+paraffins and/or C5+ diolefin monomers. These C5+ polyolefins (C5PO) may also be hydrogenated to promote stability. More preferably, these polyolefins are $C_5$-$C_{20}$ polyolefins, ever more preferably, $C_6$-$C_{20}$ polyolefins, synthesized via thermal or catalytic polymerization of coal-tar fractions, cracked petroleum distillates, terpenes or pure olefinic monomers. Aliphatic feedstreams used to produce these polyolefins are typically composed of C-5 and C-6 paraffins, olefins and diolefins, the main reactive components of which are often piperylenes such as is and trans-1,3-pentadiene. Substituted C-5 and C-6 olefins are often used as feedstreams was well.

C5PO may be found in a number of commercial products including, without limitation, those sold by Eastman Chemical Company under the trademark Eastotac® and Piccotac® resins. In one embodiment, the C5PO used is a low molecular weight thermoplastic polymer having a refractive index of less than 1.5. In another embodiment, this C5PO has a refractive index of less than 1.3. Both Eastotac and Piccotac resins can be made from monomers such as trans-1,3-pentadiene, $C_{-15}$-1,3-pentadiene, 2-mthyl-2-butene, dicyclopentadiene, cyclo-pentadiene and cyclopentene monomers. EASTOTAC resins are usually hydrogenated during manufacture of the resulting resins while the PICCOTAC resins are generally not.

Also useful as polyolefins in accordance with the present invention are PICCOLYTE® polyterpene hydrocarbon resins such as PICCOLYTE® A115, which is a polymer of alpha-pinene [CAS Reg. No. 31393-98-3] available from Hercules Inc. Resin Division, Hercules Plaza, 1313 North Market Street, Wilmington Del. 19894-0001.

In yet another embodiment, shine-enhancing polyolefin polymers include, without limitation, low molecular weight, lightly colored, inert thermoplastic resins derived from petrochemical feedstocks. Preferably, these thermoplastic polymers are also partially or fully hydrogenated. These include certain hydrogenated polycyclopentadienes and hydrogenated styrene/methylstyrene/indene copolymers sold under the trade name REGALITE. Some of the REGALITES are made from $C_8$+ monomers which include, without limitation, vinyl toluene, dicyclopentadiene, indene, alpha-methyl styrene, styrene and methyl indene. These low molecular weight hydrocarbon resins may be found in a number of commercial products including without limitation those sold by Eastman Chemical Middelburg BV, Tobias Asserlaan 5, 2517 KC Den Haag, the Netherlands, under the trademark REGALITE, PICCOTAC and EASTOTAC. A material that typifies a hydrocarbon resin that may be used in accordance with the present invention is REGALITE® R1090 hydrogenated thermoplastic resin, as described in product data sheet 65.014-E3, dated February, 2001, which describes REGALITE® R1090 as having the following characteristics.

Product Specifications

| PRODUCT SPECIFICATIONS | |
|---|---|
| Softening point, ring & ball, ° C. | 85-91 |
| Colour, Hunterlab b, | min − 1.0/max + 5.0 |
| 50% resin solids in toluene, | |
| 5 cm path length | |
| TYPICAL PROPERTIES | |
| Softening point, ring & ball, ° C. | 88 |
| Colour, Hunterlab b, | 1.0 |
| 50% resin solids in toluene, | |
| 5 cm path length | |
| Colour, Gardener, | |
| 50% resin solids in toluene, | |
| Initial | <1 |
| 24 hours at 177° C. | 4 |
| Density at 25° C., kg/dm3 | 0.98 |
| MMAP, ° C. | 74 |
| Molecular weight, size exclusion chromatography, | |
| Mw | 700 |
| Mn | 500 |
| Mw/Mn | 1.4 |
| Mz | 1100 |
| Melt viscosity, mPa · s at | |
| 120° C. | 6500 |
| 140° C. | 800 |
| 160° C. | 190 |

Other useful polyolefins of this type include REGALITE® R1125, R1100 and R9100.

Any of the polyolefin materials used herein may further include conventional additives known in the plastics industry. For example, REGALITE® R1090 hydrocarbon resin is stabilized with tetrakis [methylene(3,5-di-tert-butyl-4-hydroxyhydrocinnamate)]methane antioxidant.

In another embodiment of the invention, the shine enhancing polymers used, irrespective of their refractive index, are polyolefins that do not include appreciable amounts (greater than about 5% by weight) of alkylated polyvinyl pyrrolidone monomers, polyvinylpyrrolidone monomers or monoalkyl esters of poly(methylvinylether/maleic acid) as disclosed in U.S. Patent Application Publication No. 2002/0004054, published Jan. 10, 2002, naming Callelo et al. (see ¶¶0118-0122). In one embodiment, those polymers have a refractive index of less than 1.5.

The amount of shine-enhancing polymer in the shine-enhancing film former will depend on a number of factors including, without limitation, the polymer or mixture of polymers selected, their desired concentration, the solvent or solvent mixture, solubility, the nature of any other components that may be added to the film former or which will interact with the film former once formulated into a cosmetic or personal care composition, the process conditions such as temperature that will be used and the like.

However, in general, the amount of shine-enhancing polymer in the cosmetic compositions of the invention, measured by weight percent of the cosmetic composition (including lipsticks and lip glosses) as a whole, ranges from about 0.5 to about 80% w/w. If the amount of film former, rather than the amount of polymer is used in this calculation, this range may be slightly different as a result of the amount of solvent employed. In some embodiments of lip products, the amount of shine-enhancing polymer may range from 0.5 to about 30%. This is true for a lipstick. Between about 0.5 to about 60% of the shine-enhancing polymer is useful for a lip gloss. The upper limit, however, is generally not critical so long as an appropriate formulation is possible. In another embodiment, the lower limit for a lip product is about 3.0% w/w.

In addition to shine-enhancement, the shine-enhancing film formers of the present invention are often characterized by being generally water insoluble and/or offering excellent adherence to the skin.

The shine-enhancing film formers of the present invention may preferably be formulated by dissolving, dispersing, solubilizing, emulsifying, etc. the shine-enhancing polymers, such as C5PO, in a hydrocarbon solvent. Hydrocarbon solvents are preferred and useful hydrocarbon solvents in the practice of the invention include, but are not limited to, mineral oils, mineral solvents, mineral spirits, petroleum, petrolatum, waxes, synthetic hydrocarbons, animal oils, vegetable oils, and mixtures of various hydrogen carbons. Water and other aqueous solvents may also be possible for certain formulations in which case a solubilizer or emulsifier may also be desirable. In an embodiment, the shine-enhancing film former is formulated by dissolving a thermoplastic polyolefin in accordance with the invention, such as C5PO, in isododecane or a light paraffinic solvent. In another preferred embodiment, the shine-enhancing film former may be formulated by dissolving the C5PO in a non-hydrocarbon solvent such as amyl acetate, butyl acetate, isobutyl acetate, ethyl acetate, propyl acetate or isopropyl acetate.

The solvent and solubility conditions for formulating a shine-enhancing film former from a shine-enhancing polymer may be adjusted to prepare a composition that has the desired properties. Information regarding solubility parameters and solvents useful in the processing of specific polyolefins is available from the various manufacturers. Additional discussions of polymer solubility parameter concepts are presented in: Encyclopedia of Polymer Science and Technology, Vol. 3, Interscience, New York (1965) and Encyclopedia of Chemical Technology, Supp. Vol., Interscience, New York (1971), the disclosures of which are hereby incorporated by reference.

Shine-enhancing film formers in accordance with the present invention can be used as the only film former in a cosmetic composition where shine is desirable. However, the present invention also contemplates using any additional film former in combination with a shine-enhancing film former.

Depending on the application, the concentration or amount of shine-enhancing film former(s) in the personal care product or cosmetic composition may vary considerably. The amount of film former in the composition will depend on a number of factors including, without limitation, the film former or mixture of film formers selected, the solvent or solvent mixture, solubility, the desired degree of shine, the concentration of the shine-enhancing polymer in the film former, the nature of any other components that may be added to the composition or which will interact with the film former once formulated into a cosmetic or personal care composition, the process conditions such as temperature that will be used and the like. Unless stated otherwise, however, the amount of shine-enhancing film former used is in keeping with the amounts of film formers commonly used or known in the cosmetic and personal care industries.

For eyeliner and other eye formulations (mascara, eye pencils), the shine-enhancing polymer or mixture of shine-enhancing polymers preferably may vary from about 5 to about 70% w/w of the total composition, and more preferably from about 20 to about 70% w/w of the total composition.

In another embodiment of the present invention, the shine-enhancing film former or mixture of shine-enhancing film formers may be combined in a formulation with an additional film former or mixture of additional film formers. Although additional film formers as defined herein are non-shine-enhancing film formers, the additional film formers of the present invention are not necessarily unable to enhance shine. The additional film former(s) may improve, but are not limited to improving, smoothness or spreadability, water-resistance, transfer resistance properties, or other properties as would be expected by one of skill in the art.

The amount of additional film former in the composition, if any, will depend on a number of factors including, without limitation, the additional film former or mixture of additional film formers selected, the concentration in the solvent of any polymer, the solvent or solvent mixture, its solubility, the desired degree of shine, the amount of shine-enhancing film formers used and the type thereof, the nature of any other components that may be added to the composition or which will interact with the additional film former once formulated into a cosmetic or personal care composition, the process conditions such as temperature that will be used and the like.

In general, the amount of additional film former(s) added to supplement or replace the shine-enhancing film formers in a composition may vary between 0 and about 80% by weight, with the understanding that at least some shine-enhancing film former is necessary to provide improved shine. This is in addition to the amount of shine-enhancing film formers used. However, the total amount of all film formers used in cosmetic or personal care products should not exceed about 90% w/w.

Examples of preferred additional film formers that may be used in the practice of the invention include: vinylpyrrolidone/vinyl acetate (PVPNA) copolymers such as the Luviskol VA grades (all ranges) from BASF® Corporation and the PVPNA series from ISP; acrylic fluorinated emulsion film formers including Foraperle® film formers such as Foraperle® 303 D from Elf Atochem although Foraperle® may not be preferable for some cosmetic formulations; GANEX® copolymers such as Butylated PVP, PVP/Hexadecene copolymer, PVP/Eicosene copolymer or tricontanyl; poly (vinylpyrrolidonel-diethylaminoethyl methacrylate) or PVP/Dimethyl-aminoethylmethacrylate copolymers such as Copolymer 845; Resin ACO-5014 (Imidized IB/MA copolymer); other PVP based polymers and copolymers; Silicone gums; Cyclomethicone and Dimethicone crosspolymers (For example, Dow Corning® 2-9040, See U.S. Pat. No. 5,654,362, the disclosure of which is hereby incorporated by reference); trimethyl siloxysilicates such as SR 1000, SS4230, or SS4267 available from GE Silicones; alkyl cycloalkylacrylate copolymers (See WO 98/42298 the disclosure of which is hereby incorporated by reference); or Mexomere® film formers and other allyl stearate/vinyl acetate copolymers (allyl stearate/VA copolymers); Polyolprepolymers such as PPG-12/SMDI copolymer, Polyolprepolymers such as PPG-12/SMDI copolymer, Poly(oxy-1,2-ethanediyl), α-hydro-ω-hydroxy-polymer with 1,1'-methylene-bis-(4-isocyanatocyclohexane) available from Barnet; Avalure™ AC Polymers (Acrylates Copolymer) and Avalure™ UR polymers (Polyurethane Dispersions), available from BFGoodrich.

Additional film formers which also may be used within the framework of the invention include any film former known in the art such as: PVP, acrylates, and urethanes; synthetic polymers of the polycondensate type or free-radical type, or ionic type, polymers of natural origin and mixtures thereof or any other film formers known within the practice of the cosmetic and pharmaceutical arts which one skilled in the art may determine to be compatible.

In another embodiment, the additional film formers are block copolymers. For example, the block copolymers may be of the types described in U.S. Published Application No. 2002/0110573 (published Aug. 15, 2002), particularly 0011-0014, incorporated herein by reference in its entirety.

The di-block, tri-block, multi-block and/or radial or star block copolymer additional film formers used may contain at least two thermodynamically incompatible segments. A di-block is usually defined as an A-B type or a hard segment (A) followed by a soft segment (B) in sequence. A tri-block is usually defined as an A-B-A type copolymer or a ratio of one hard, one soft, and one hard segment. Multiblock or radial or star copolymer film formers usually contain any combination of hard and soft segments, provided that there are both hard and soft characteristics. An example of a hard block copolymer segment is styrene, while examples of soft block copolymer segments are ethylene, propylene, and butylene or combinations thereof.

The block copolymer additional film formers may be chosen from the class of Kraton® rubbers (Shell Chemical Company) or from similar gelling agents. In one embodiment, the copolymer additional film former comprises Kraton® rubbers that are present in a gel in amounts from about 10 to about 20% concentration by weight. Kraton® rubbers are thermoplastic elastomers in which the polymer chains comprise a tri-block, di-block, or radial or star block configuration or numerous mixtures thereof. The Kraton® tri-block rubbers have polystyrene segments on each end of a rubber segment, while the Kraton® di-block rubbers have a polystyrene segment attached to a rubber segment. The Kraton® radial or star configuration, in a further preferred embodiment, may be a four-point or other multipoint star made of rubber with a polystyrene segment attached to each end of a rubber segment. The configuration of each of the Kraton® rubbers form separate polystyrene and rubber domains.

Each molecule of Kraton® rubber is said to comprise block segments of styrene monomer units and rubber monomer and/or co-monomer units. The most common structure for the Kraton® triblock copolymer is the linear A-B-A block type styrene-butadiene-styrene, styrene-isoprene-styrene, or styrene-ethylenebutylene-styrene. The Kraton® di-block is preferably the AB block type such as styrene-ethylenepropylene, styrene-ethylenebutylene, styrene-butadiene, or styrene-isoprene. The Kraton® rubber configuration is well known in the art and any block copolymer film former with a similar configuration may also be used as an additional film former.

Other block copolymer additional film formers include a styrene/butylene/ethylene/styrene copolymer (tri-block), an ethylene/propylene/styrene copolymer (radial or star block) or a mixture or blend of the two. (Some manufacturers refer to block copolymers as hydrogenated block copolymers, e.g. hydrogenated styrene/butylene/ethylene/styrene copolymer (tri-block) or hydrogenated ethylene/propylene/styrene copolymer (radial or star block), all of which are within the scope of the invention.) Specific examples include Versagel M5960, or Versagel M5970, all of which are available from Penreco of Houston Tex. and block copolymers available from Brooks Industries, such as Gel Base.

Additional film formers may also include film formers produced using appreciable amounts of polymers or copolymers having alkylated polyvinyl pyrrolidone monomers, polyvinylpyrrolidone monomers or monoalkyl esters of poly (methyl vinyl ether/maleic acid) such as those disclosed in U.S. Patent Application Publication No. 2002/004054, published Jan. 10, 2002, naming Calello et al., (see ¶¶ 0118-0122).

Spherical compounds may also be used for spreadability and smoothness, these include, without limitation, polyurethane such as BPD 500, nylon 12, silica, polymethyl methacrylates and other acrylates or methacrylates and their esters, and other microspheres. Non-limiting examples of film formers useful for water and transfer-resistance properties are described in U.S. Published Application No. 2002/0110573, (published Aug. 15, 2002), incorporated herein by reference in its entirety, particularly, but not limited to, p. 1-2, ¶ 7-14.

In a preferred embodiment of the present invention, a cosmetic product is formulated in the form of a water-in-oil emulsion or an oil-in-water emulsion. While at least one of the shine-enhancing film former and any additional film formers may be in the water or in the oil phase, maximum efficacy has been demonstrated when they are formulated in the oil phase. Thus, in a preferred embodiment, at least one of the shine-enhancing film formers and/or at least one additional film former is in the oil phase. Where a plurality of film formers, shine enhancing and/or otherwise are used, they may also be disposed individually or as a mixture in different phases. In other embodiments of the invention, at least one additional film former may be in the oil phase or the water phase, or there may be at least one additional film former in both the water and oil phases.

The water phase of the emulsion generally uses deionized water as a dispersing medium and may include added electrolytes. The oil phase of the emulsion generally contains surfactants, solvents or cosolvents and any fillers, pigments and/or rheological additives.

Products, particularly those in the form of emulsions, may contain a surfactant or other emulsifier as a formulation aid to help disperse the components throughout the emulsion medium. For example, organic and organosilicone emulsifiers may be used for water-in-oil systems. Examples of organic emulsifiers include any ethoxylated surfactants known in the art such as Polysorbate-20, Laureth-7, and Laureth4. Examples of organosilicone emulsifiers include cetyl dimethicone copolyol-polyglyceryl-4-isostearate-hexylaurate (ABIL WE 09) available from Goldschmidt Chemical Corporation, Cetyl Dimethicone Copolyol (ABIL® EM 90), (ABIL® EM 97), Laurylmethicone Copolyol (5200), Cyclomethicone and Dimethicone Copolyol (DC 5225 C) available from GE silicones, Cyclopentasiloxane & Dimethicone Copolyol (GE SF 1528) or any other formulation aids, including fatty substances, known by one of skill in the art.

The compositions of the invention may include thickeners, fatty substances and/or waxes and other structuring agents (collectively "structuring agents") generally used in personal care and/or cosmetic compositions or other formulation aids. These are generally used in the creation of cosmetic compositions that will have a self-sustaining structure at room temperature such as a lipstick, lip pencil, lip liner, eye pencil or eye shadow. Of course, it is possible to use these same types of materials as viscosity modifiers as discussed herein, such as when making a lip gloss. However, when used as a viscosity modifier rather than a structuring agent, the amount used should be insufficient to provide a cosmetic composition that is self-sustaining structurally at room temperature (18° C.-25° C.).

Thickeners in accordance with the present invention include those disclosed in U.S. Published Patent Application No. 2004 0096472 A1 published May 20, 2004, to Florence Tournilhac, the text of which, as it relates to thickeners, is hereby incorporated by reference. These include fatty acid esters of dextrins. Other traditional thickeners may be used as well.

Thickening agents may also include, for example, clays, or organoclays, silicas, cellulose derivatives; hectorites; synthetic polymers such as an acrylic polymer or an associative polymer of the polyurethane type; gums and in particular xanthan gum. These may be used in the amounts described for other structuring agents.

Representative fatty substances include silicones in esterified or unesterified liquid form or in esterified solid form, such as behenate dimethicone, polyamide resins, nonsilicone fatty substances, such as oils, pastes and vegetable, mineral, animal and/or synthetic waxes. Waxes, for example, may be used to form a non-transparent composition. As used herein, a "wax" may be any lipophilic fatty compound which is soluble in the liquid fatty phase, unlike most fillers or pigments. The at least one wax, for example, may have a melting point greater than about 45°, such as, for example greater than about 55° C. Non-limiting examples of such waxes include waxes of natural origin, such as beeswax, carnauba wax, candelilla wax, ouricury wax, Japan wax, cork fiber wax, sugar cane wax, paraffin waxes, lignite wax, microcrystalline waxes, lanolin wax, montan wax and ozokerites, hydrogenated oils such as hydrogenated jojoba oil, jojoba esters, waxes of synthetic origin, such as polyethylene waxes derived from polymerization of ethylene, waxes obtained by Fischer-Tropsch synthesis, fatty acid esters and glycerides, and silicone waxes such as derivatives of poly(di)methylsiloxane. Any amount of a structuring agent may be used as long as it imparts a self-supporting structure. In particular, structuring agents may be used in an amount of up to about 30% w/w, more preferably 20% w/w.

In gloss and ointment like products, such as lip gloss or eye make-up applied with a brush or pad, a viscosity modifier may be used. Like "structuring agents" as used herein, "viscosity increasing agent" or "viscosity modifier" (used synonymously herein) is a functional term meant to convey that the resulting product is generally a viscous cream, ointment, paste or powder, but is not sufficiently viscous to have a self-sustaining structure such as a stick, pencil or liner. Viscosity increasing agents include, without limitation, polyamide resin, silica, silica dimethyl silylate, triisostearin, triisononanoin, trihydroxystearin, modified natural starch, stearamide, 12-hydroxy stearic acid, dimethicone crosspolymer, dimethicone copolyol crosspolymer, monodibenzylidence sorbitol, N-lauryl-L-glutamate and mondibenzylidene sorbitol. It will be appreciated that structuring agents can provide viscosity modification as well. However, if these are used in addition to, or in place of, traditional viscosity increasing agents, they will be used in these cosmetic compositions in amounts that are insufficient, in a given formulation, to provide a self-sustaining structure such as a stick, liner, pencil or an eye shadow. Generally, a gloss or similar cosmetic composition in accordance with the invention will have a viscosity of less than about 300,000 cP at 25° C., while a lipstick or eye shadow or other self-sustaining structure and cosmetic composition will have a viscosity that is greater than about 300,000 cP at 25° C. As used herein, viscosity is determined on a Brookfield Helipath RVT Viscometer using a T-F Spindle at 10 rpm and at 25° C. For a lip gloss, and indeed for non-structured cosmetics in accordance with the present invention, (e.g. not a pencil, solid liner or stick) viscosity can range from about 95,000 to 300,000 cP (also sometimes abbreviated "c.p.s."), more preferably, especially for lip gloss, 200,000 to 300,000 cp. The amount of viscosity increasing agent used will generally range from about 0.1 to about 20% w/w. If structuring agents are used, the amount will range from about 0.5 to about 10% w/w. This, of course, depends upon the overall formulation.

Any other additive, excipient or active ingredient used in cosmetic or personal care products may also be added to the composition of the invention. Indeed, since the shine-enhancing film formers of the present invention may be used to replace some or all of the film formers used in existing or future formulations, any ingredients of a cosmetic or personal care product, contemplated for use in a film-former-containing product is acceptable. These include gels or gelling agents, oils, waxes, preservatives, thickening agents, cosmetic oils, moisturizing agents, solvents or cosolvents, surfactants, emollients, dyes, pigments, coloring agents, conventional shine enhancers, buffers, fragrances and conditioners, spreading agents; structuring agents; dispersants; preservatives, in particular water-soluble preservatives; antifoaming agents; wetting agents; UV-screening agents or UV filters; perfumes; fillers; cosmetic or pharmaceutical active agents; topical coatings; moisturizers; vitamins and derivatives thereof; biological materials and derivatives thereof used in conventional amounts, such as from 0-20% by weight of the finished formulation.

The composition of the invention may additionally include any additive usually employed in the field envisaged such as antioxidants, perfumes, essential oils, stabilizers, cosmetic active substances, vitamins, essential fatty acids, lipophilic sunscreens, minerals, liposoluble polymers, and especially hydrocarbon polymers such as polyalkylenes and polyacrylates. All of these may be used in at least conventional amounts.

The person skilled in the art will of course take care to choose the optional additional compounds and/or their quantity in such a way that the advantageous properties of the composition according to the invention are not, or are substantially not, impaired by the envisaged addition.

The compositions of the present invention may also be effective in waterproofing. The compositions may therefore minimize washoff of the active or functional ingredients. The compositions may also retard dehydration of the skin by forming an occlusive film and reducing trans epidermal water loss. Such materials are generally present, if at all, in an amount of from about 0.5-30% by weight based on the final weight of the formulation (w/w).

Emollients that may preferably be used in the compositions of the invention include glycerin, propylene glycol, cyclomethicone, dimethicone, and emollients and other similar ingredients disclosed in the International Cosmetic Dictionary and Handbook Vol 2., more particularly the emollients disclosed on pages 1656-1661. The disclosure of the International Cosmetic Dictionary and Handbook Vol 2. is hereby incorporated by reference. In one embodiment, emollients are present at a concentration of about 0.5% to about 75% w/w. In another embodiment, the emollients are present in an amount of about 1% to about 60% w/w.

In a preferred embodiment, the compositions can provide a barrier between the skin and the environment, entrapping in between the active and/or functional ingredients. The preferred composition and the barrier formed by said composition may boost the activity of the functional ingredients such as the SPF and UV light protection and/or block the effect of the humidity and the environment.

In pigmented products, the ratio of shine-enhancing film formers and additional film formers can be adjusted for best adherence to the skin or hair and water resistance. An important consideration is the ratio of pigments to the amount of film formers. A pigment should be understood to mean inorganic or organic, white or colored particles. Pigments that may be used in the practice of the invention include titanium dioxide, D & C Red No. 7 Calcium Lake, D & C Red No. 21 Aluminum Lake, Iron Oxides, FD & C Yellow No. 5 Aluminum Lake, FD & C Blue no. 1 Aluminum Lake and any other pigment or treated pigment known in the cosmetic arts such as 0.1 to about 30% w/w.

Fillers and mothers-of-pearl may also be added to said formulations to modify the texture of the composition and the matteness/gloss effect. Fillers should be understood to mean lamellar or nonlamellar, inorganic or synthetic, colorless or white particles. Mothers-of-pearl should be understood to mean iridescent particles produced especially by certain mollusks in their shell or else synthesized. Pearling agents that may be used in the practice of the invention include mica, iron oxides, titanium dioxide and any other pearling agent known in the cosmetic arts such as 0.1 to about 20% w/w.

The shine-enhancing film formers of the present invention may be used to add or preserve shine in cosmetic compositions in which shine is desired. More preferably, the shine-enhancing film formers are used in compositions for cosmetics. In a most preferred embodiment, the shine-enhancing film formers comprise a composition for lipstick or lip gloss with high shine.

The compositions of the invention may provide increased shine without decreased transfer-resistance in a broad range of applications. These applications include pigmented cosmetics, including lip products, mascaras, eye liners, eye shadows, sunscreen containing cosmetic products, etc. The products of the present invention can particularly be useful in any cosmetic application where shine is a desired property.

In one exemplary embodiment of the present invention, shine-enhancing film formers are used in a cosmetic composition for the lips. The composition of the present invention may increase the glossy appearance of lip product.

A make-up composition for the lips according to the invention makes it possible to obtain a homogeneous film which has high shine, a light texture and remains comfortable to wear throughout the day. The preferred film is also not tacky or sticky, while being soft, supple, elastic and flexible on the skin. The film may have very good retention, no transfer, no migration, and no stain.

In another exemplary embodiment of the present invention, shine-enhancing film formers are used in a cosmetic composition for mascara. The composition of the present invention may increase the glossy appearance of mascara.

A preferred embodiment of mascara comprises at least one shine-enhancing film former of the invention and an allyl stearate/vinyl acetate copolymer additional film former such as a Mexomere™ film former. In a further preferred embodiment, a Mexomere™ film former is present in a concentration of about 0.5 to about 10% w/w.

In another exemplary embodiment of the present invention, shine-enhancing film formers are used in a cosmetic composition for eyeliner products. The composition of the present invention may increase the glossy appearance of eyeliner.

A preferred embodiment of eyeliner comprises the shine-enhancing film formers of the invention and at least one allyl stearate/vinyl acetate copolymer film former. In a further preferred embodiment, the allyl stearate/vinyl acetate copolymer film former is a Mexomere™ film former. In a another preferred embodiment, a Mexomere™ film former is present in a concentration of about 0.5% to about 3.5% w/w.

In addition, eyeliners of the present invention may also include at least one of hydrocarbon gels or bentone type gels, waxes such as beeswax, carnauba wax and derivatives thereof, preservatives, and other ingredients such as propylene carbonate, isododecane, silica, silica silylate, petroleum distillates, polyethylene, preservatives, and pigments such as iron oxides, ultramarines, and black oxides. Another embodiment would further comprise at least one bentone type gel, such as Gel SS71, Gel EA2786, Quaternium-18 Bentonite, 38 CE, Gel ISD V or Gel ISD. The concentration of Bentone type gel preferably may range from less than about 1% to about 50% w/w, preferably 0.5 to about 20% w/w.

The packaging and application device for any subject of the present invention may be chosen and manufactured by persons skilled in the art on the basis of their general knowledge, and adapted according to the nature of the composition to be packaged. Indeed, the type of device to be used may be in particular linked to the consistency of the composition, in particular to its viscosity; it may also depend on the nature of the constituents present in the composition, such as the presence of volatile compounds.

EXAMPLE 1

High Shine Lipstick

| Trade Name | CTFA Name | % |
|---|---|---|
| | A | |
| Eastotac H-100W | Hydrogenated C6-20 polyolefin | 5.0 |
| | Octyldodecanol | 12.85 |
| | Isopropyl lanolate | 9.82 |
| | Acetylated lanolin | 9.82 |
| | Phenyltrimethicone | 4.36 |
| | Diisostearyl malate | 13.38 |
| | Lanolin oil | 9.82 |
| | Tridecyl trimellitate | 10.86 |
| | BHT | 0.05 |
| | B | |
| | waxes | 15.2 |
| | C | |
| | pigments | 2.34 |
| | D | |
| | Pearls and filler | 5.5 |
| | E | |
| | actives | 1.0 |

Manufacturing Procedure:
1. Combine all the ingredients of Phase A into the Mixing Kettle. Heat to 85° C.-95° C. under medium agitation and mix for 20-30 minutes.
2. Charge a portion of the oil phase (Phase A) into the Disconti Mill. Heat to (around) 65° C.
3. Add the pigments (Phase C). Mill for 40-45 min. @ 60-65° C. Check the dispersion.
4. Melt the waxes (Phase B) @ 100-105° C. in the melting kettle
5. Discharge the color phase from the mill.
6. Rinse the mill with the remaining oil phase for 20-30 min.
7. Complete the color phase with the rinse residual.
8. Add the color phase into the melting kettle. Heat to 100° C.-105°
9. Mix for 20-30 minutes.
10. Add Phase D (Pearls if applicable). Mix 20-30 minutes or until homogeneous.
11. Lower the temperature of the batch between 82° C.-85° C. Add Phase E (Active Phase). Mix 10-20 minutes or until homogeneous.
12. Pour the batch into a mold.

EXAMPLE 2

Lipstick

| Trade Name | CTFA Name | % |
|---|---|---|
| | A | |
| | octyldodecanol | 11.00 |
| | Isopropyl lanolate | 9.66 |
| | Acetylated lanolin | 9.66 |
| | phenyltrimethicone | 4.29 |
| | Diisostearyl malate | 13.16 |
| | Lanolin oil | 9.66 |
| | Tridecyl trimellitate | 10.48 |
| | BHT | 0.05 |
| Piccolyte A115 | Polyterpene | 5.0 |
| | B | |
| Waxes | Polyamide resin; Polyethylene; Hydrogenated coco-glycerides; Hydrogenated castol oil | 18.2 |

-continued

| Trade Name | CTFA Name | % |
|---|---|---|
| | C | |
| Pigments | | 2.34 |
| | D | |
| Fillers | | 5.5 |
| | E | |
| Actives | Vitamins; *Aloe* leaf extract; Jojoba seed oil; "flower" fruit oil | 1.0 |

*the same basic procedure used in Example 1 may be used in producing a lipstick from the above ingredients.

EXAMPLE 3

Lipstick

| Trade Name | CTFA Name | % |
|---|---|---|
| | A | |
| | octyldodecanol | 9.82 |
| | Isopropyl lanolate | 9.80 |
| | Acetylated lanolin | 9.80 |
| | phenyltrimethicone | 6.50 |
| | Diisostearyl malate | 9.63 |
| | Lanolin oil | 9.80 |
| | Tridecyl trimellitate | 10.64 |
| | BHT | 0.05 |
| Lexorez 200 | Hexanedioic acid, polymer with 1,2,3-propanetriol and 2,2,4-trimethyl-1,3-pentanediol | 7.0 |
| | B | |
| Waxes | | |
| Eastotac H-100W | Hydrogenated C6-20 polyolefin | 4.0 |
| | Polyethylene; Hydrogenated coco-glycerides; Microcrystalline Wax | 13.86 |
| | C | |
| | Pigments | 2.1 |
| | D | |
| | Fillers | 5.5 |
| | E | |
| Actives | Vitamins; *aloe* leaf extract; jojoba seed oil; "flower" fruit oil | 1.5 |

*the same basic procedure used in Example 1 may be used in producing a lipstick from the above ingredients.

EXAMPLE 4

| Seq | Trade Name | INCI Name | |
|---|---|---|---|
| A | | Hydrogenated Polyisobutene | 13.55 |
| | BHT | BHT | 0.04 |
| | | Caprylic/Capric/Stearic Triglyceride | 8.10 |
| | | Bis-diglyceryl Polyacladipate-2 | 12.00 |
| | | Diisostearyl Malate | 5.00 |
| | | Triisononanoin | 7.8 |
| | | Tridecyl Trimellitate | 10.00 |
| | Ganex V 216 | PVP/Hexadecene Copolymer | 5.00 |
| B | REGALITE R 1090 | Hydrogenated styrene/methyl styrene/indene copolymer | 5.00 |
| | | Polyethylene; Hydrogenated Coco-glycerides | 14.40 |
| C | | Pigments | 3.59 |
| | | Diisopropyl dimer dilinoleate | 6.00 |
| D | | Filler | 7.0 |
| E | Active phase | | 2.53 |
| | | TOTAL = | 100.00 |

*the same basic procedure used in Example 1 may be used in producing a lipstick from the above ingredients.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A colored cosmetic composition having enhanced shine, comprising:
   hydrogenated polycyclopentadiene;
   hydrogenated polyisobutene;
   an organic solvent; and a coloring agent.

2. The cosmetic composition of claim 1, wherein said hydrogenated polycyclopentadiene is present in an amount of about 0.5 to about 80% by weight of said composition.

3. The cosmetic composition of claim 1, wherein said hydrogenated polyisobutene is present in an amount up to 20% by weight of said composition.

4. The cosmetic composition of claim 1, wherein said organic solvent comprises a hydrocarbon solvent.

5. The cosmetic composition of claim 4, wherein said hydrocarbon solvent comprises isododecane.

6. The cosmetic composition of claim 1, wherein said coloring agent comprises a dye or pigment.

7. The cosmetic composition of claim 1, which is an emulsion, suspension, dispersion or a solution.

8. A method of instilling shine and wearability to skin, lips, eyelashes or hair, comprising applying to skin, lips, eyelashes or hair, a colored cosmetic composition comprising hydrogenated polycyclopentadiene; hydrogenated polyisobutene; an organic solvent; and a coloring agent.

* * * * *

UNITED STATES PATENT AND TRADEMARK OFFICE
CERTIFICATE OF CORRECTION

| | | |
|---|---|---|
| PATENT NO. | : 7,611,726 B2 | Page 1 of 1 |
| APPLICATION NO. | : 10/891549 | |
| DATED | : November 3, 2009 | |
| INVENTOR(S) | : Wei Hong Yu | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1502 days.

Signed and Sealed this

Twelfth Day of October, 2010

David J. Kappos
*Director of the United States Patent and Trademark Office*